United States Patent [19]

Nakashima et al.

[11] Patent Number: 5,523,440
[45] Date of Patent: Jun. 4, 1996

[54] SILACYCLOHEXANE COMPOUND, A METHOD OF PREPARAING IT AND A LIQUID CRYSTAL COMPOSITION CONTAINING IT

[75] Inventors: Mutsuo Nakashima; Takaaki Shimizu; Tsutomu Ogihara; Takeshi Kinsho; Tatsushi Kaneko, all of Kubiki-Mura; Hideshi Kurihara, Kawasaki, all of Japan

[73] Assignee: Shin-Etsu Chemical Co., Ltd., Tokyo, Japan

[21] Appl. No.: 388,307

[22] Filed: Feb. 14, 1995

[30] Foreign Application Priority Data

Feb. 18, 1994 [JP] Japan .................. 6-045117

[51] Int. Cl.⁶ .................... C07F 7/08
[52] U.S. Cl. ............ 556/406; 252/299.01; 252/299.63; 252/299.66
[58] Field of Search .......... 556/406; 252/299.01, 252/299.63, 299.66

[56] References Cited

U.S. PATENT DOCUMENTS 4,826,984  5/1989  Berlin et al. .................. 556/406 X
4,973,723  11/1990  Cawthon et al. ................ 556/406

FOREIGN PATENT DOCUMENTS 0355008  8/1989  European Pat. Off. .
0632044  6/1994  European Pat. Off. .
0630903  6/1994  European Pat. Off. .

*Primary Examiner*—Paul F. Shaver
*Attorney, Agent, or Firm*—Townsend & Banta

[57] ABSTRACT

There is provides a silacyclohexane compound and method of making same. The silacyclohexane compound has the following formula (1):

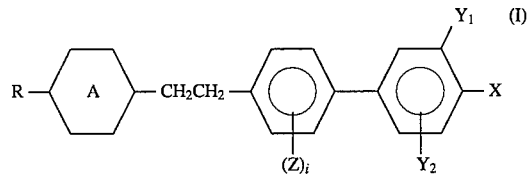

wherein R denotes a linear-chain alkyl group with a carbon number of 1–10, a branched-chain alkyl group with a carbon number of 3–8, an alkoxyalkyl group with a carbon number of 2–7, a mono- or di-fluoroalkyl group with a carbon number of 1–10, or an alkenyl group with a carbon number of 2–8, and

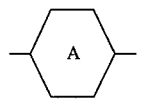

denotes a trans-1-sila-1,4-cyclohexylene or a trans-4-sila-1,4-cyclohexylene group whose silicon at position 1 or position 4 has a substitutional group(s) of H, F, Cl or $CH_3$, X denotes H, CN, F, Cl, $CF_3$, $OCF_3$, $CF_2Cl$, CHFCl, $OCHF_2$, $OCF_2Cl$, OCHFCl, R or OR group, Z denotes F, and i denotes 0, 1 or 2.

7 Claims, No Drawings

SILACYCLOHEXANE COMPOUND, A METHOD OF PREPARAING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it, as well as a liquid crystal display element which contains said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required in all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and latent liquid crystal compounds. Because of this, it is also important that components of a liquid crystal composition mix easily.

Among liquid crystal compounds which can be components for these, one of the basic components conventionally known which controls the electro-optical performance is a compound which has a so-called cyclohexyl ring-ethylene-phenyl ring-phenyl ring structure (BECH structure) such as those shown below.

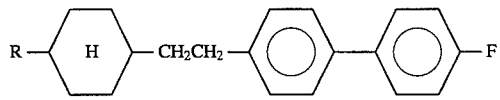

(See Japanese examined patent publication Tokko Sho 59-35900.)

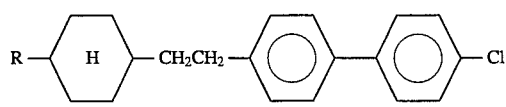

(See Japanese examined patent publication Tokko Sho 59-35900.)

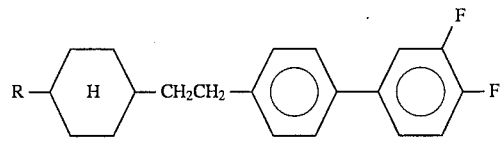

(See Japanese examined patent publication Tokko Hei 3-22855.)

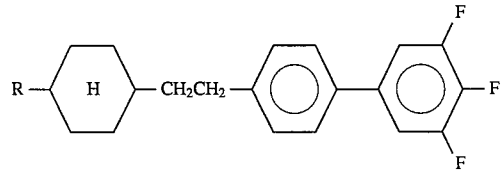

(See Japanese unexamined patent publication Tokkai Hei 2-233626.)

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

This invention is a newly developed liquid crystal substance targeting improvement in the characteristics of liquid crystal substances, and its object is to provide a liquid crystal compound containing silacyclohexane rings, which is completely different from the conventional liquid crystal compounds with cyclohexyl ring-ethylene-phenyl ring-phenyl ring structures (BECH structures).

This invention provides a silacyclohexane compound represented by the following general formula (I).

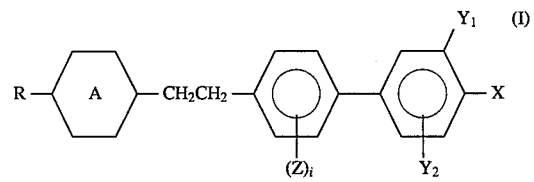

In the above formula, R denotes a linear-chain alkyl group with a carbon number of 1–10, a branched-chain alkyl group with a carbon number of 3–8, an alkoxyalkyl group with a carbon number of 2–7, a mono- or di-fluoroalkyl group with a carbon number of 1–10, or an alkenyl group with a carbon number of 2–8.

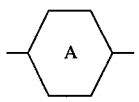

denotes a trans-1-sila-1,4-cyclohexylene or a trans-4-sila-1,4-cyclohexylene group whose silicon at position 1 or position 4 has a substitutional group(s) of H, F, Cl or $CH_3$. X denotes H, CN, F, Cl, $CF_3$, $OCF_3$, $CF_2Cl$, $CHFCl$, $OCHF_2$, $OCF_2Cl$, $OCHFCl$, R or OR, $Y_1$ and $Y_2$ independently denote H, F, Cl, CN or $CH_3$. Z denotes F. i denotes 0, 1 or 2.

This invention also provides a method of preparing the silacyclohexane compound as represented by the general formula (I) characterized by the use of a carbon-carbon bond formation reaction or a carbon-silicon bond formation reaction between an organometallic reagent R-M and

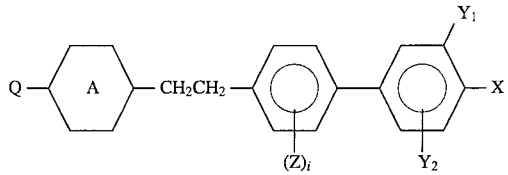

(M denotes MgP (P denotes a halogen atom), ZnP or Li, and Q denotes a halogen atom, or an alkoxy, methanesulfonyl, benzenesulfonyl, p-toluenesulfonyl or trifluoromethanesulfonyl group).

This invention also provides a method of preparing the silacyclohexane compound as represented by the general formula (I) characterized by the use of a carbon-carbon bond formation reaction or a carbon-silicon bond formation reaction between an organometallic reagent

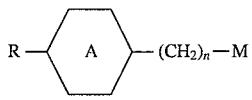

and

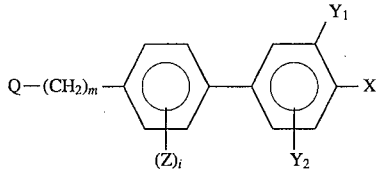

(n and m are both the integers 0, 1 or 2, where n+m=2).

This invention also provides a method of preparing the silacyclohexane compound as represented by the general formula (I) characterized by the use of a carbon-carbon bond formation reaction or a carbon-silicon bond formation reaction between an organometallic reagent

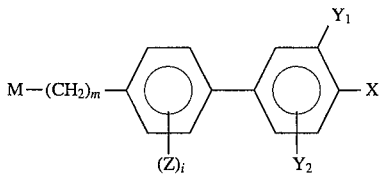

and

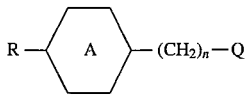

This invention also provides a method of preparing the silacyclohexane compound as represented by the general formula (I) characterized by the use of a carbon-carbon bond formation reaction between an organometallic reagent

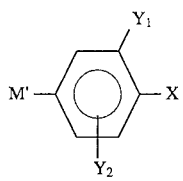

(M' denotes M or $B(OR')_2$ (R' denotes a methyl group or a H atom)) and

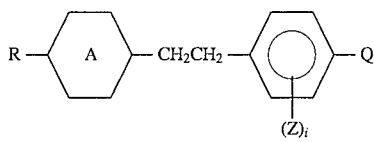

This invention also provides a method of preparing the silacyclohexane compound as represented by the general formula (I) characterized by the use of a carbon-carbon bond formation reaction between an organometallic reagent

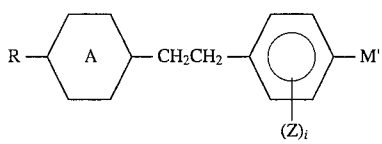

and

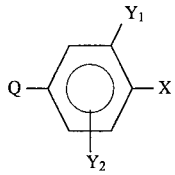

This invention also provides a liquid crystal composition characterized by containing the silacyclohexane compound described in claim 1 and a liquid crystal display element which contains said liquid crystal composition.

DETAILED DESCRIPTION

This invention is described in detail below.

Specifically, the new compounds represented by said general formula (I) are silacyclohexane compounds represented by the ring structures shown below:

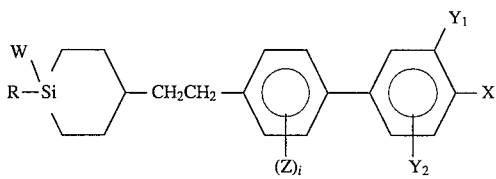

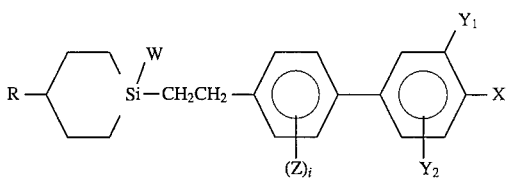

R denotes the following groups listed in (a) through (e):

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (c) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl or ethoxypentyl group (d) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluoroocryl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluoroocryl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluoroburyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl-8,8-difluorooctyl, 8,8-difluorononyl, 8,8-difluorodecyl, 9,9-difluorononyl or 10,10-difluorodecyl group (e) An alkenyl group with a carbon number of 2–8, i. e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W denotes a H, F, Cl or $CH_3$ group. X denotes H, CN, F, Cl, $CF_3$, $OCF_3$, $CF_2Cl$, $CHFCl$, $OCHF_2$, $OCF_2Cl$, $OCHFCl$, R or OR. $Y_1$ and $Y_2$ independently denote H, F, Cl, CN or $CH_3$. Z denotes F. i denotes 0, 1 or 2.

Specific examples of

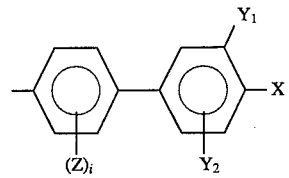

follow.

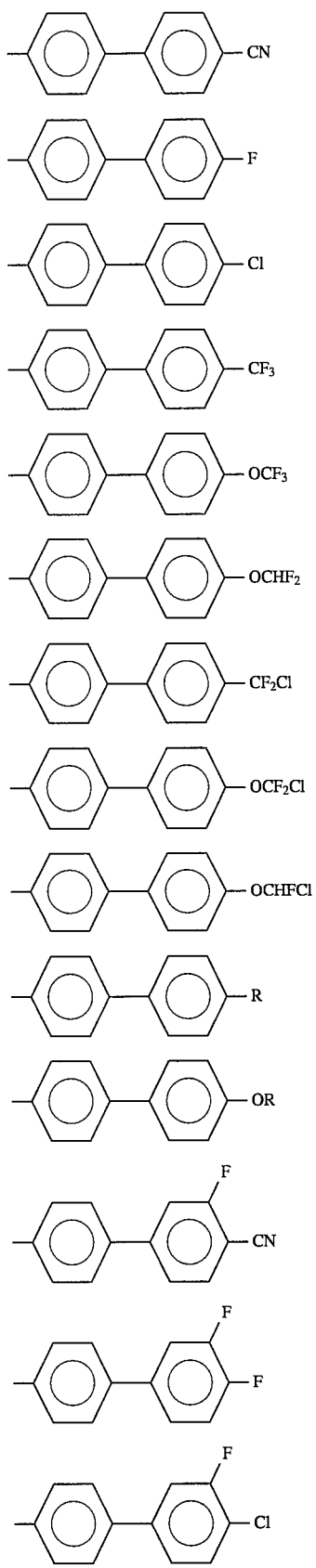

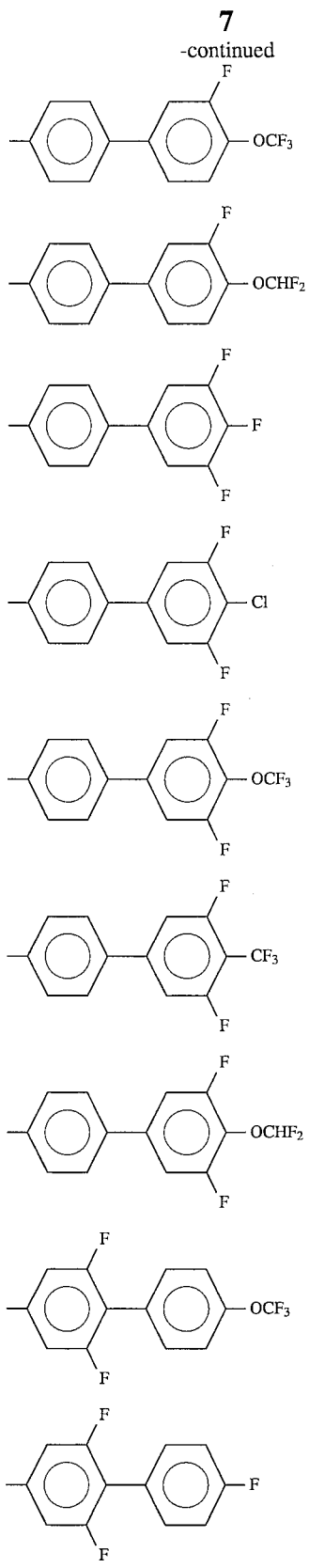
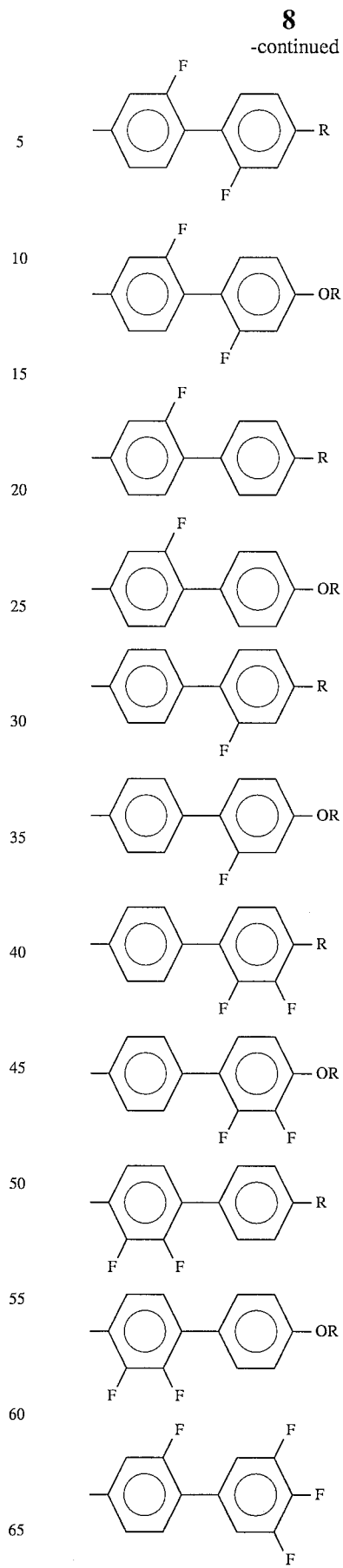

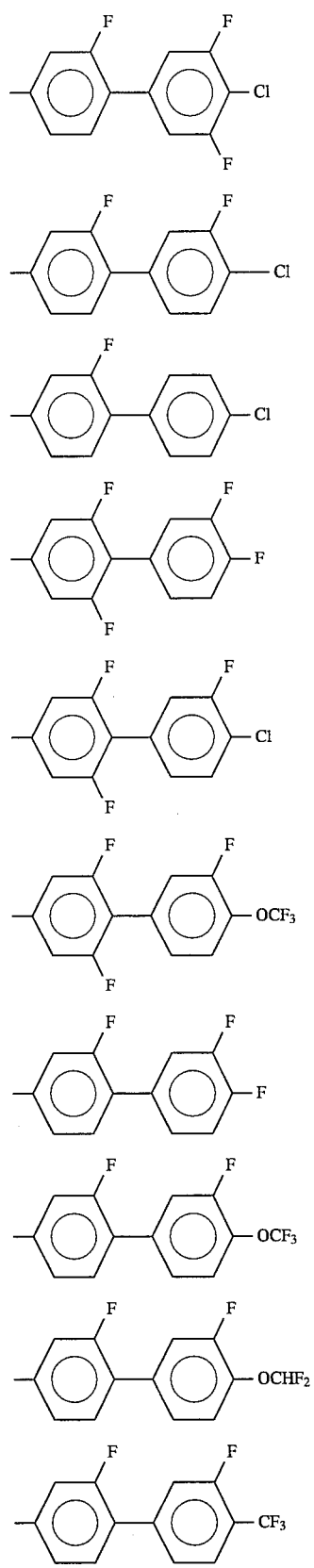
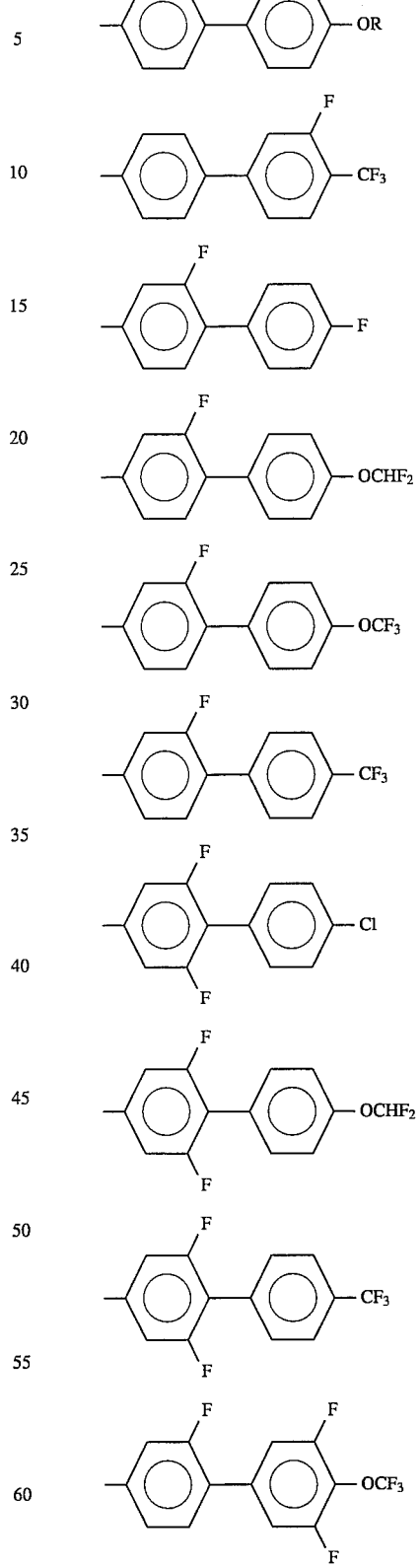

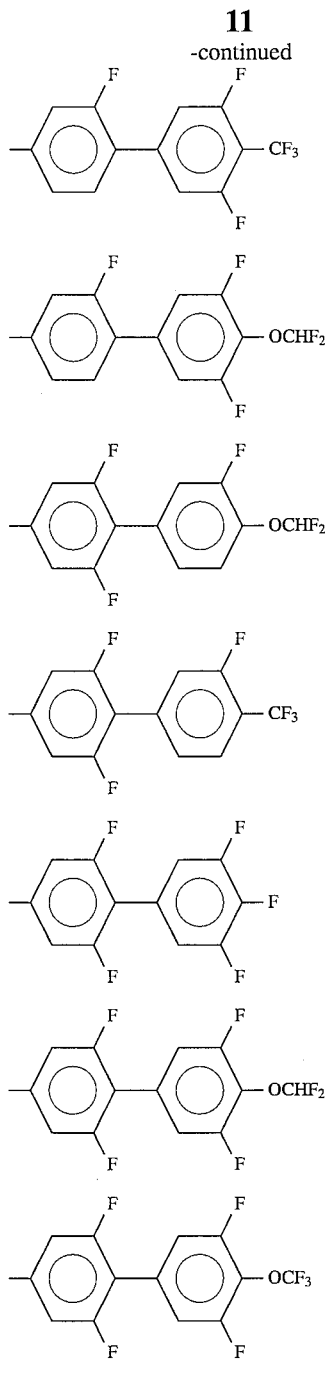

Of these,

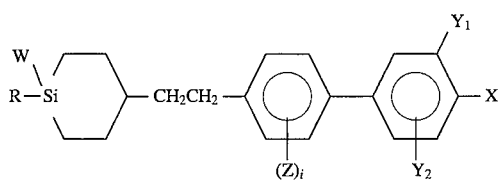

is preferable for the ring structure.

For R, the following groups listed in (f) through (j) are desirable for practical use:

(f) A linear-chain alkyl group with a carbon number of 2–7, i.e. an ethyl, n-propyl, n-butyl, n-pentyl, n-hexyl or n-heptyl group (g) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (h) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (i) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups (j) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and $CH_3$ groups are desirable for W in practical use.

F, Cl, Br, I, $OCH_3$ or $OC_2H_5$ are preferable for Q.

The following are preferable for

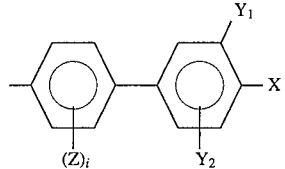

in practical use.

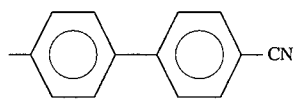

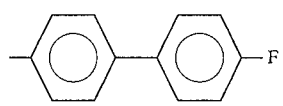

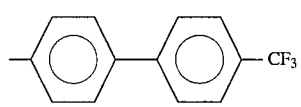

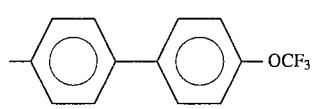

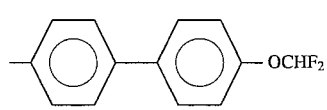

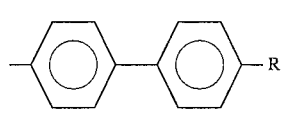

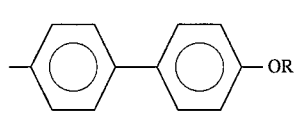

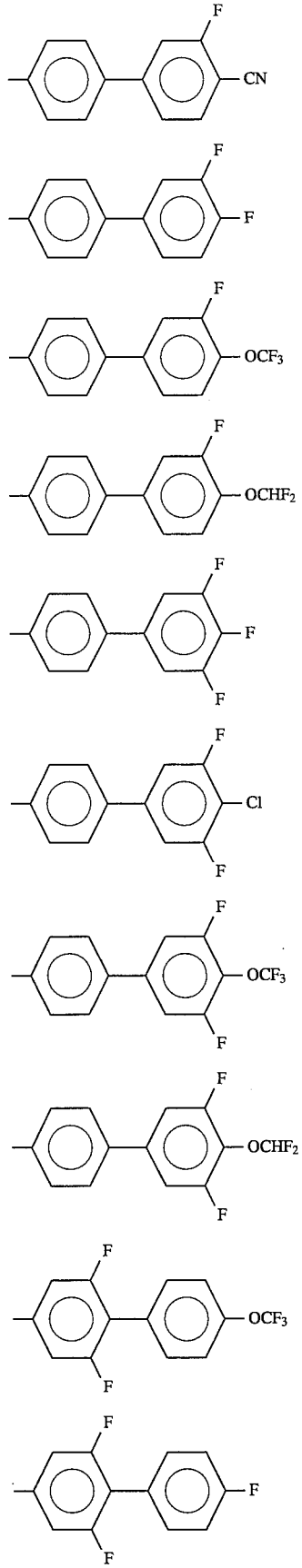
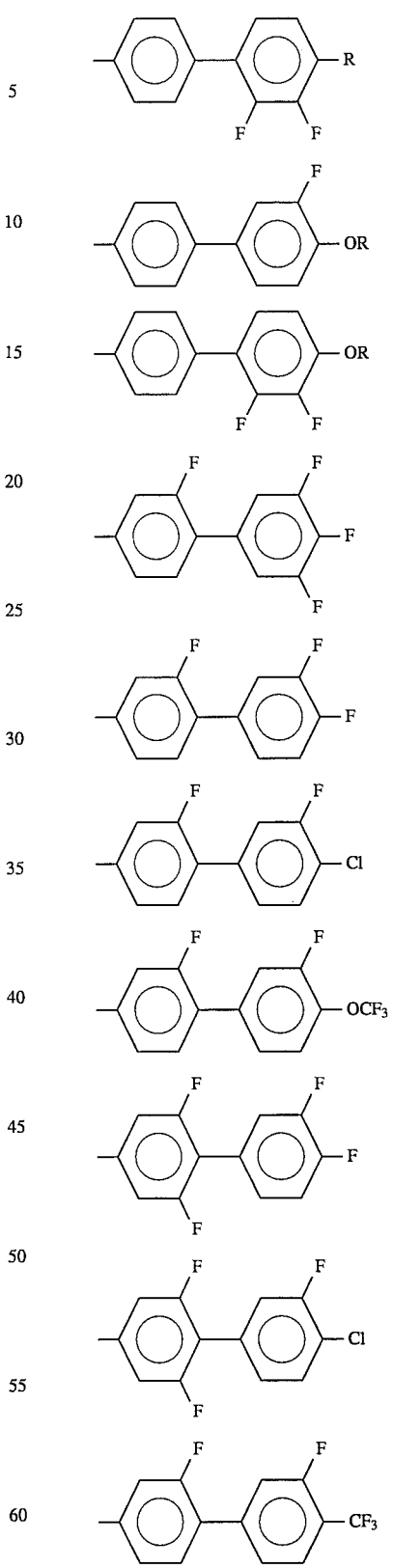

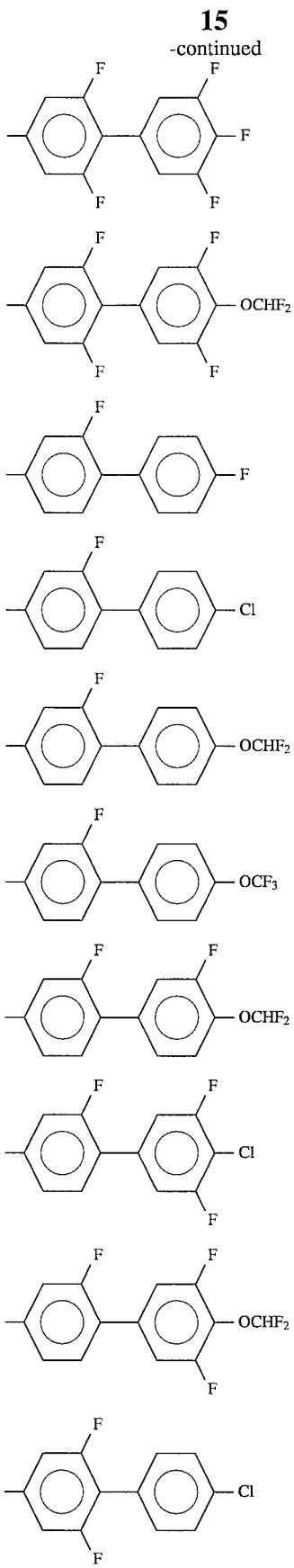
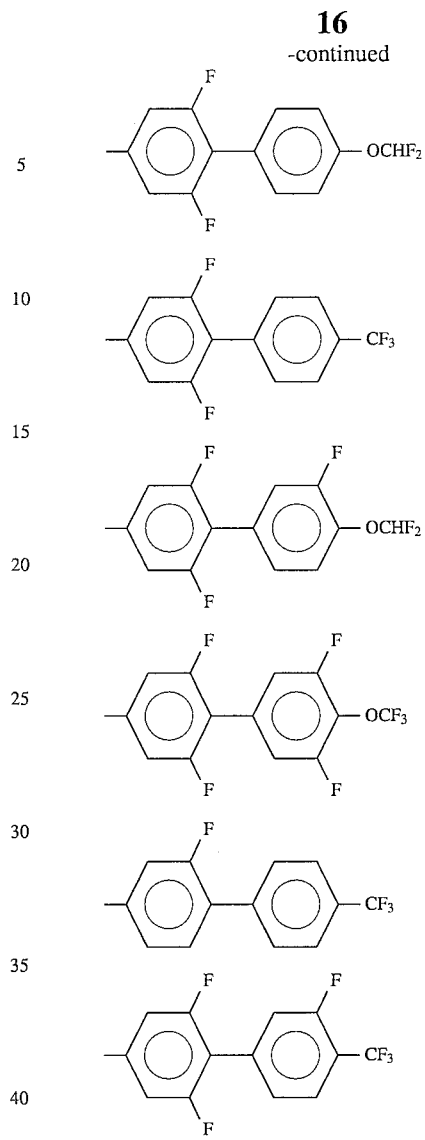

The manufacturing methods of these compounds are described next. Although the reaction substrates are somewhat different depending on the ring structure, all of them are prepared using the organometallic reagent coupling reactions shown below.

In the reaction between an organometallic reagent R-M and

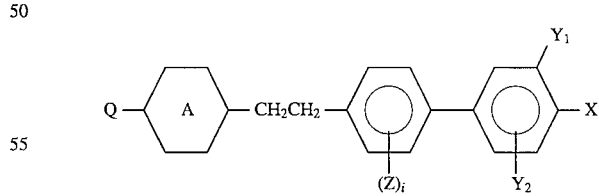

(M denotes MgP (P denotes a halogen atom), ZnP or Li, and Q denotes a halogen atom, or an alkoxy, methanesulfonyl, benzenesulfonyl, p-toluenesulfonyl or trifluoromethanesulfonyl group), when

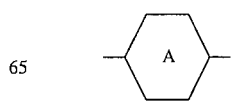

is

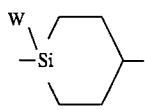

(W denotes H, F, Cl or a CH$_3$ group), Q is a halogen atom or an alkoxy group, for example. Particularly, if Q is Cl, Br, or an OCH$_3$ or OCH$_2$CH$_3$ group, then the carbon-silicon bond formation reaction proceeds easily and gives a high yield of the target product.

When

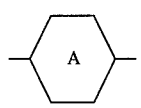

is

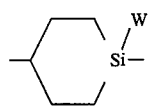

this carbon-carbon bond formation reaction is carried out in the presence of a catalytic amount of copper salt. In this case, Q is a halogen atom or a sulfonyl group, for example. It is particularly preferable if Q is Br, I or a p-toluenesulfonyl group because then the target product can be obtained with a high yield.

In the reaction between an organometallic reagent

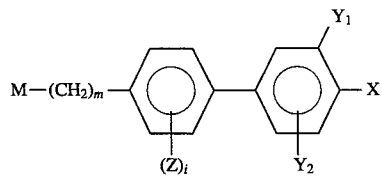

and

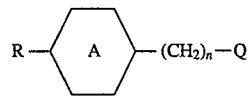

if

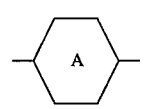

is

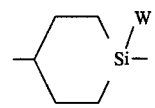

and n= 0, then Q is a halogen atom or an alkoxy group, for example. Particularly, if Q is Cl, Br, or an OCH$_3$ or OCH$_2$CH$_3$ group, then the carbon-silicon bond formation reaction proceeds easily and gives a high yield of the target product.

Also, if

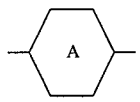

is

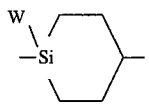

or

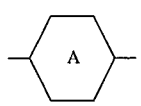

is

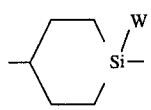

and n= 1 or 2, then these carbon-carbon bond formation reactions are carried out in the presence of a catalytic amount of copper salt. In this case, Q is a halogen atom or a sulfonyl group, for example. It is particularly preferable if Q is Br, I or a p-toluenesulfonyl group because then the target product can be obtained with a high yield.

In the reaction between an organometallic reagent

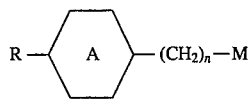

and

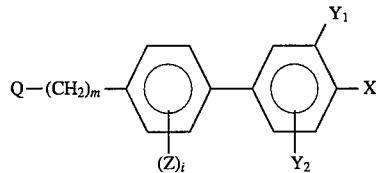

if n= 0 or 1 in

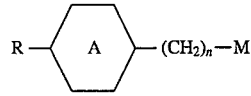

then these carbon-carbon bond formation reactions are carried out in the presence of a catalytic amount of copper salt. Q is a halogen atom or a sulfonyl group, for example. It is particularly preferable if Q is Br, I or a p-toluenesulfonyl group because then the target product can be obtained with a high yield.

If n= 2 in

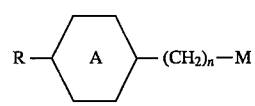

then this reaction is carried out in the presence of a transition metal catalyst. Palladium compounds and nickel compounds are particularly preferable for the catalyst. Q is a halogen atom or a sulfonyl group, for example. It is particularly preferable if Q is Cl, Br or I because then the target product can be obtained with a high yield.

The reaction between an organometallic reagent

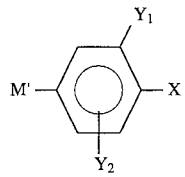

and

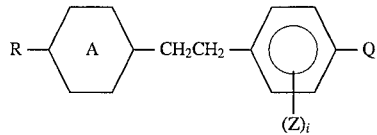

is carried out in the presence of a transition metal catalyst. Palladium compounds and nickel compounds are particularly preferable for the catalyst. Q is a halogen atom or a sulfonyl group, for example. It is particularly preferable if Q is Cl, Br or I because then the target product can be obtained with a high yield.

The reaction between an organometallic reagent

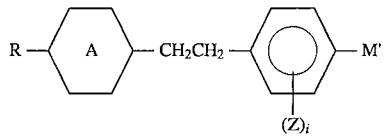

and

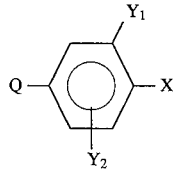

is carried out in the presence of a transition metal catalyst. Palladium compounds and nickel compounds are particularly preferable for the catalyst. Q is a halogen atom or a sulfonyl group, for example. It is particularly preferable if Q is Cl, Br or I because then the target product can be obtained with a high yield.

Since the compound produced here is a mixture of trans isomers and cis isomers in terms of the configuration of the silacyclohexane ring, a conventional purification means such as chromatography and recrystallization is employed to separate and purify the trans isomers to obtain the silacyclohexane compound of this invention represented by the general formula (I).

The silacyclohexane compound of this invention can be mixed with known compounds to obtain a liquid crystal composition. The specific compound used for mixing to obtain the liquid crystal compound can be chosen from among the known compounds shown below:

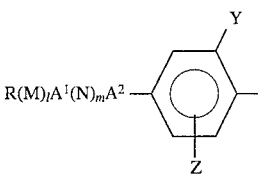

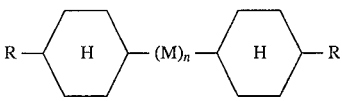

In the above formulas, (M) and (N) denote one of the following:

1) A trans-1,4-cyclohexylene group which has no substitution or which has one or more substitutional groups such as F, Cl, Br, CN or alkyl groups 2) A ring obtained by substituting O or S for one or nonadjacent two $CH_2$ groups in the cyclohexane ring 3) A 1,4-cyclohexenylene group 4) A 1,4-phenylene group which has no substitution or which has one or two substitutional groups such as F, Cl, $CH_3$ or CN groups 5) A ring obtained by substituting an N atom for one or two CH groups in a 1,4-phenylene group.

$A^1$ and $A^2$ denote —$CH_2CH_2$—, —CH=CH—, —C≡C—, —$CO_2$—, —OCO—, —$CH_2O$—, —$OCH_2$— or a single bond.

l, m=0, 1 or 2 (where l+m=1, 2 or 3, and n=0, 1 or 2).

R denotes hydrogen, a linear-chain alkyl group with a carbon number of 1–10, a branched-chain alkyl group with a carbon number of 3–8, an alkoxyalkyl group with a carbon number of 2–7 or an alkenyl group with a carbon number of 2–8.

X denotes H, CN, F, Cl, $CF_3$, $OCF_3$, $OCHF_2$, $CF_2Cl$, $OCF_2Cl$, $OCHFCl$, R or OR. Y and Z denotes F.

In the above description, if l=2 and n=2, then (M) can contain heterogeneous rings, and if m=2, then (N) can contain heterogeneous rings.

The ratio of one or more types of the silacyclohexane compounds of this invention contained in the liquid crystal composition is 1–50 wt %, more preferably 5–30 wt %. The liquid crystal composition can also contain a polygenetic dye(s) to generate a colored guest-host system and additives to change the dielectric anisotropy, viscosity and the orientation of the nematic phase.

The liquid crystal composition thus obtained can be used to manufacture various liquid crystal displays using conventional methods. That is, the liquid crystal composition containing the silacyclohexane compound of this invention is sealed between transparent base plates which have electrodes of desired shapes and thus used as liquid crystal display elements. This element can have various undercoatings, overcoatings for the orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the guest-host (GH) method and the polymer dispersion (PDLC) method can be adopted.

As described thus far, the liquid crystal compound of this invention, when used as a component of a liquid crystal composition, can increase the refractive index while minimizing an increase in the viscosity of the whole system, and provides a conventionally unknown and completely new liquid crystal compound silacyclohexane ring with a silicon atom(s) in its molecular structure. The liquid crystal compound whose substitutional group X in the general formula (I) is not R or OR provides, in addition to the advantages described above, a compound whose dielectric anisotropy, $\Delta\epsilon$, is positive and relatively large.

EXAMPLE

The details of this invention are described below by referring to specific examples.

Example 1

Preparation of 4-[2-(trans-4-n-propyl-4-silacyclohexyl) ethyl]-4'-fluorobiphenyl 2.5 g (20 mmol) of n-propyl bromide was dripped into a mixture of 0.5 g (21 mmol) of magnesium and 50 ml of tetrahydrofuran (hereafter abbreviated as "THF") to obtain a Grignard's reagent. This solution was then dripped into a 50 ml THF solution of 6.7 g (20 mmol) of 4-[2-(trans-4-chloro-4-silacyclohexyl)ethyl]-4'-fluorobiphenyl to obtain 4-[2-(trans-4-n-propyl-4-silacyclohexyl) ethyl]-4'-fluorobiphenyl. The silacyclohexane rings of this product were a mixture of trans isomers and cis isomers. After a conventional after treatment, they were separated by means of chromatography to obtain 6.1 g of the trans isomers (yield 90%).

The following silacyclohexane compounds shown in Examples 2–5 were obtained in the same manner as Example 1.

Example 2

4-[2-(trans-4-n-butyl-4-methyl-4-silacyclohexyl) ethyl]-3',5'-difluoro-4'-chlorobiphenyl

Example 3

4-[2-(trans-4-n-pentyl-4-silacyclohexyl) ethyl]-2,2'-difluoro-4'-n-propoxybiphenyl

Example 4

4-[2-(trans-4-n-propyl-4-silacyclohexyl) ethyl]-3',4',5'-trifluorobiphenyl

Example 5

4-[2-(trans-4-n-pentyl-4-fluoro-4-silacyclohexyl)ethyl]-4'-difluorochloromethylbiphenyl

Example 6

Preparation of 4-[2-(trans-4-(1-propenyl)-4-silacyclohexyl)ethyl]-3',4'-difluorobiphenyl 4.7 g (20 mmol) of trans-1-(1-propenyl)-4-bromomethyl-1-silacyclohexane was dripped into a mixture of 0.5 g (21 mmol) of magnesium and 50 ml of THF to obtain a Grignard's reagent. This solution was then dripped into a 50 ml THF solution of 5.7 g (20 mmol) of 4'-bromomethyl-3,4-difluorobiphenyl and a catalytic amount of cuprous chloride to obtain 4-[2-(trans-4-(1-propenyl)-4-silacyclohexyl) ethyl]-3',4'-difluorobiphenyl. The silacyclohexane rings of this product were a mixture of trans isomers and cis isomers. After a conventional after treatment, they were separated by means of chromatography to obtain 6.1 g of the trans isomers (yield 86%).

The following silacyclohexane compounds shown in Examples 7 and 8 were obtained in the same manner as Example 6.

Example 7

4-[2-(trans-4-n-pentyl-4-silacyclohexyl)ethyl]-2,6-difluoro-4'-trifluoromethoxybiphenyl

Example 8

4-[2-(trans-4-n-propyl-4-silacyclohexyl) ethyl]-2,3',4',5'-tetrafluorobiphenyl

Example 9

Preparation of 4-[2-(trans-4-n-pentyl-4-silacyclohexyl) ethyl]-3',4'-difluorobiphenyl 5.7 g (20 mmol) of 4'-bromomethyl-3,4-difluorobiphenyl was dripped into a mixture of 0.5 g (21 mmol) of magnesium and 50 ml of THF to obtain a Grignard's reagent. This solution was then dripped into a 50 ml THF solution of 5.3 g (20 mmol) of trans-1-n-pentyl-4-bromomethyl-1-silacyclohexane and catalytic amounts of cuprous chloride and triethyl phosphite to obtain 4-[2-(trans-4-n-pentyl-4-silacyclohexyl)ethyl-3,40 ,4'-difluorobiphenyl. The silacyclohexane rings of this product were a mixture of trans isomers and cis isomers. After a conventional after treatment, they were separated by means of chromatography to obtain 7.0 g of the trans isomers (yield 91%).

IR (liquid film) ν max: 2920, 2850, 2100, 1605, 1504, 1311, 1267 and 814 cm$^{-1}$ C-N transition point: 38.6° C., N-I transition point: 58.2° C.

The following silacyclohexane compounds shown in Examples 10–13 were obtained in the same manner as Example 9.

Example 10

4-[2-(trans-4-n-propyl-4-silacyclohexyl)ethyl]-4'-chlorobiphenyl

Example 11

4-[2-(trans-4-n-pentyl-4-silacyclohexyl)ethyl]-4'-trifluoromethoxybiphenyl

Example 12

4-[2-(trans-4-n-propyl-4-silacyclohexyl)ethyl]-4'-n-pentylbiphenyl

Example 13

4-[2-(trans-4-n-propyl-4-silacyclohexyl) ethyl]-2,6,4'-trifluorobiphenyl

Example 14

Preparation of 4-[2-(trans-4-isobutyl-4-silacyclohexyl) ethyl]-3'-fluoro-4'-chlorobiphenyl 5.3 g (20 mmol) of trans-1-isobutyl-4-(2-bromoethyl)-1-silacyclohexane was dripped into a mixture of 0.5 g (21 mmol) of magnesium and 50 ml of THF to obtain a Grignard's reagent. This solution was then dripped into a 50 ml THF solution of 5.7 g (20 mmol) of 4'-bromo-3-fluoro- 4-chlorobiphenyl and a catalytic amount of tetrakis (triphenylphosphine) palladium (0) to obtain 4-[2-(trans-4-isobutyl-4-silacyclohexyl)ethyl]-3'-fluoro-4'-chlorobiphenyl. The silacyclohexane rings of this product were a mixture of trans isomers and cis isomers. After a conventional after treatment, they were separated by means of chromatography to obtain 6.2 g of the trans isomers (yield 80%).

The following silacyclohexane compounds shown in Examples 15 and 16 were obtained in the same manner as Example 14.

Example 15

4-[2-(trans-4-n-pentyl-4-silacyclohexyl) ethyl]-2,6,3'-trifluoro-4'-trifluoromethoxybiphenyl

Example 16

4-[2-(trans-4-n-pentyl-4-silacyclohexyl) ethyl]-4'-trifluoromethylbiphenyl

Example 17

Preparation of 4-[2-(trans-4-n-propyl-4-silacyclohexyl)ethyl]-3',4'-difluorobiphenyl 6.5 g (20 mmol) of 1-[2-(trans-4-n-propyl-4-silacyclohexyl)ethyl]-4-bromobenzene was dripped into a mixture of 0.5 g of magnesium (21 mmol) and 50 ml of THF to obtain a Grignard's reagent. This solution was then dripped into a 50 ml THF solution of 3.9 g (20 mmol) of 3,4-difluoro-1-bromobenzene and a catalytic amount of (1,3-bis (diphenylphosphino) propane) nickel chloride (II) to obtain 4-[2-(trans-4-n-propyl-4-silacyclohexyl) ethyl]-3',4'-difluorobiphenyl. The silacyclohexane rings of this product were a mixture of trans isomers and cis isomers. After a conventional after treatment, they were separated by means of chromatography to obtain 5.9 g of the trans isomers (yield 83%).

IR (KBr method) ν max: 2924, 2852, 2087, 1603, 1506, 1308, 1279 and 814 $cm^{-1}$ C-N transition point: 50.8° C., N-I transition point: 59.1° C.

The following silacyclohexane compounds shown in Examples 18 and 19 were obtained in the same manner as Example 17.

Example 18

4-[2-(trans-4-n-pentyl-4-methyl-4-silacyclohexyl)ethyl]-2-fluoro-4'-n-propylbiphenyl

Example 19

4-[2-(trans-4-(1-propenyl)-4-silacyclohexyl) ethyl]-4'-difluoromethoxybiphenyl

Example 20

Preparation of 4-[2-(trans-4-(3-methoxypropyl)-4-silacyclohexyl)ethyl]-3',4'-fluorobiphenyl 3.9 g (20 mmol) of 3,4-difluoro-1-bromobenzene was dripped into a mixture of 0.5 g (21 mmol) of magnesium and 50 ml of THF to obtain a Grignard's reagent. This solution was dripped into a 20 ml THF solution of 2.8 g (20 mmol) of zinc chloride to obtain an organozinc reagent. This solution was then dripped into a 50 ml THF solution of 7.1 g (20 mmol) of 1-(2-(trans-4-(3-methoxypropyl)-4-silacyclohexyl) ethyl]-4-bromobenzene and a catalytic amount of tetrakis (triphenylphosphine) palladium (0) to obtain 4-[2-(trans-4-(3-methoxypropyl)-4-silacyclohexyl)ethyl]-3',4'-fluorobiphenyl. The silacyclohexane rings of this product were a mixture of trans isomers and cis isomers. After a conventional after treatment, they were separated by means of chromatography to obtain 6.5 g of the trans isomers (yield 84%).

The following silacyclohexane compounds shown in Examples 21–24 were obtained in the same manner as Example 20.

Example 21

4-[2-(trans-4-n-pentyl-4-silacyclohexyl)ethyl]-4'-cyanobiphenyl

Example 22

4-[2-(trans-4-n-propyl-4-silacyclohexyl)ethyl]-2,6,3'-trifluoro-4'-chlorobiphenyl

Example 23

4-[2-(trans-4-(4-fluorobutyl)-4-silacyclohexyl)ethyl]-2',3'-difluoro-4'-ethoxybiphenyl

Example 24

4-[2-(trans-4-(4-fluoropentyl)-4-silacyclohexyl)ethyl]-2',3'-difluoro-4'-n-propylbiphenyl

Example 25

Preparation of 4-[2-(trans-4-n-pentyl-1-silacyclohexyl) ethyl]-4'-fluorobiphenyl 5.6 g (20 mmol) of 4-(2-bromoethyl)-4'-fluorobiphenyl was dripped into a mixture of 0.5 g (21 mmol) of magnesium and 50 ml of THF to obtain a Grignard's reagent. This solution was then dripped into a 50 ml THF solution of 4.1 g (20 mmol) of trans-1-chloro-4-pentyl-1-silacyclohexane to obtain 4-[2-(trans-4-n-pentyl-1-silacyclohexyl) ethyl]-4'-fluorobiphenyl. The silacyclohexane rings of this product were a mixture of trans isomers and cis isomers. After a conventional after treatment, they were separated by means of chromatography to obtain 7.0 g of the trans isomers (yield 95%).

The following silacyclohexane compounds shown in Examples 26–31 were obtained in the same manner as Example 25.

Example 26

4-[2-(trans-4-n-pentyl-1-silacyclohexyl) ethyl]-2,2'-difluoro-4'-n-propylbiphenyl

Example 27

4-[2-(trans-4-(3-methoxypropyl)-1-silacyclohexyl)ethyl]-2'-fluoro-4'-ethoxybiphenyl

Example 28

4-[2-(trans-4-n-pentyl-1-silacyclohexyl)ethyl]-2-fluoro-4'-fluorochloromethoxybiphenyl

Example 29

4-[2-(trans-4-isobutyl-1-methyl-1-silacyclohexyl)ethyl]-4'-n-pentoxybiphenyl

Example 30

4-[2-(trans-4-n-pentyl-1-silacyclohexyl)ethyl]-3',5'-difluoro-4'-difluoromethoxybiphenyl

Example 31

4-[2-(trans-4-n-pentyl-1-silacyclohexyl)ethyl]-3'-fluoro-4'-cyanobiphenyl

Example 32

A liquid crystal mixture A comprising 40% of 4-(trans-4-(trans-4-ethylcyclohexyl) cyclohexyl)-1,2-difluorobenzene, 35% of 4-(trans-4-(trans-4-propylcyclohexyl)cyclohexyl)-1,2-difluorobenzene and 25% of 4-(trans-4-(trans-4-pentylcyclohexyl) cyclohexyl)-1,2-difluorobenzene exhibits the following characteristics:

Δn (refractive index @589 nm and 25° C.)=0.0800

Δε(dielectric anisotropy @1 kHz and 25° C.)=4.60

ζ (viscosity @20° C.)=25.5 cp

A mixture comprising 85% of this mixture A and 15% of the 4-[2-(trans-4-n-pentyl-4-silacyclohexyl)ethyl]-3',4'-difluorobiphenyl obtained in Example 9 has an effect of increasing the refraction index Δ n while minimizing an increase in the viscosity:

Δn (589 nm, 25° C.)= 0.0920

Δε(1 kHz, 25 ° C.)= 4.65

ζ (viscosity @20° C.)= 26.0 cp

We claim:

1. A silacyclohexane compound represented by the following formula (1):

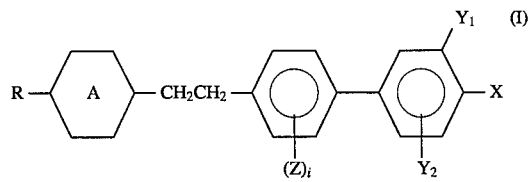

wherein R denotes a linear-chain alkyl group with a carbon number of 1–10, a branched-chain alkyl group with a carbon number of 3–8, an alkoxyalkyl group with a carbon number of 2–7, a mono- or di-fluoroalkyl group with a carbon number of 1–10, or an alkenyl group with a carbon number of 2–8, and

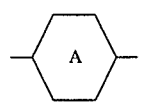

denotes a trans-1-sila-1,4-cyclohexylene or a trans-4-sila-1,4-cyclohexylene group whose silicon at position 1 or position 4 has a substitutional group(s) of H, F, Cl or $CH_3$, Z denotes H, CN, F, Cl, $CF_3$, $OCF_3$, $CF_2Cl$, $CHFCl$, $OCHF_2$, $OCF_2Cl$, $OCHFCl$, R or OR, $Y_1$ and $Y_2$ independently denote H, F, Cl, CN or $CH_3$, Z denotes F, and i denotes 0, 1 or 2.

2. A method of preparing the silacyclohexane compound as described in claim 1, wherein a carbon-carbon bond formation reaction or a carbon-silicon bond formation reaction is used between an organometallic reagent R-M, and

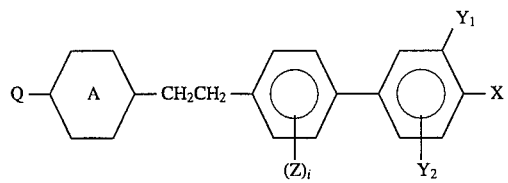

wherein M denotes MgP, P denotes a halogen atom, ZnP or Li, and Q denotes a halogen atom, or an alkoxy, methanesulfonyl, benzenesulfonyl, p-toluenesulfonyl or trifluoromethanesulfonyl group.

3. A method of preparing the silacyclohexane compound as described in claim 1, wherein a carbon-carbon bond formation reaction or a carbon-silicon bond formation reaction is used between an organometallic reagent

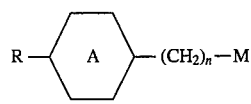

and

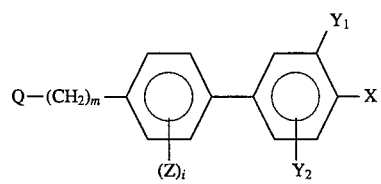

wherein n and m are both the integers 0, 1 or 2, where n+ m 2; M denotes MgP, P denotes a halogen atom, ZnP or Li, and Q denotes a halogen atom, or an alkoxy, methanesulfonyl, benzenesulfonyl, p-toluenesulfonyl or trifluoromethanesulfonyl group.

4. A method of preparing the silacyclohexane compound as described in claim 1, wherein a carbon-carbon bond formation reaction or a carbon-silicon bond formation reaction is used between an organometallic reagent

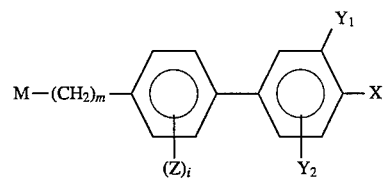

and

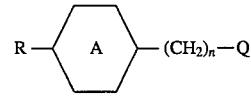

wherein M denotes MgP, p denotes a halogen atom, ZnP or Li, and O denotes a halogen atom, or an alkoxy, methanesulfonyl, benzenesulfonyl, p-toluenesulfonyl or trifluoromethanesulfonyl group.

5. A method of preparing the silacyclohexane compound as described in claim 1, wherein a carbon-carbon bond formation reaction is used between an organometallic reagent

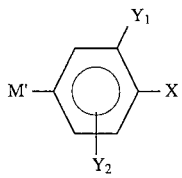

wherein M' denotes M or B(OR')$_2$, R' denotes a methyl group or an H atom, M denotes MgP, P denotes a halogen atom, ZnP or Li, and

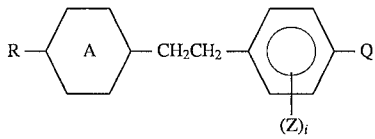

wherein O denotes a halogen atom, or an alkoxy, methanesulfonyl, benzenesulfonyl, p-toluenesulfonyl or trifluoromethanesulfonyl group.

6. A method of preparing the silacyclohexane compound as described in claim 1, wherein a carbon-carbon bond formation reaction between an organometallic reagent

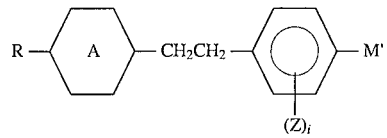

and

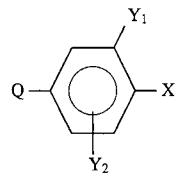

wherein M' denotes M Or B (OR')$_2$, M denotes a halogen atom, ZnP or Li, R' denotes a methyl group or an H atom, and O denotes a halogen atom, or an alkoxy, methanesulfonyl benzenesulfonyl, p-toluenesulfonyl or trifluoromethanesulfonyl group.

7. A liquid crystal composition comprising the silacyclohexane compound of claim 1.

* * * * *